United States Patent [19]

Roberts

[11] Patent Number: 5,119,807
[45] Date of Patent: *Jun. 9, 1992

[54] PRESSURIZED MEDICAL VENTILATION SYSTEM

[75] Inventor: Josephine A. Roberts, 7509 Ben Avon Rd., Bethesda, Md. 20817; Jephthae W. Burwell, Wash., D.C.

[73] Assignee: Josephine A. Roberts, Bethesda, Md.

[*] Notice: The portion of the term of this patent subsequent to Feb. 21, 2006 has been disclaimed.

[21] Appl. No.: 349,216

[22] Filed: May 9, 1989

Related U.S. Application Data

[63] Continuation-in-part of Ser. No. 311,959, Feb. 17, 1989, which is a continuation-in-part of Ser. No. 74,867, Jul. 17, 1987, Pat. No. 4,805,609.

[51] Int. Cl.[5] .............. A61M 11/06; A62B 9/02; A62B 7/10; A62B 23/02
[52] U.S. Cl. .................. 128/200.24; 128/200.21; 128/203.12; 128/204.16; 128/205.12; 128/205.24; 128/205.27; 239/304; 239/338
[58] Field of Search ............ 128/200.14, 200.21, 128/200.22, 203.12, 203.14, 203.19, 204.14, 204.18, 205.12, 205.24, 205.27, 912, 200.24, 204.16; 239/338, 343, 352, 370, 304, 320, 104, 124; 604/83, 85, 187, 218

[56] References Cited

U.S. PATENT DOCUMENTS

| 1,061,539 | 5/1913 | Haertel | 128/203.19 |
|---|---|---|---|
| 2,696,210 | 12/1954 | Hickman | 128/200.21 |
| 3,123,071 | 3/1964 | Felts | 128/203.12 |
| 3,172,406 | 3/1965 | Bird et al. | 128/200.18 |
| 3,213,966 | 10/1965 | Veres et al. | 239/338 |
| 3,276,472 | 10/1966 | Jinkens et al. | 604/83 |
| 3,473,530 | 10/1969 | Urbanowicz | 239/338 |
| 3,545,677 | 12/1970 | Power | 239/338 |
| 3,630,196 | 12/1971 | Bird et al. | 128/200.18 |
| 3,881,480 | 5/1975 | Lafourcade | 128/200.21 |
| 3,968,812 | 7/1976 | Eross | 128/205.12 |
| 4,020,834 | 5/1977 | Bird | 128/205.12 |
| 4,279,250 | 7/1981 | Valenta et al. | 128/200.22 |
| 4,405,308 | 9/1983 | Jessup | 128/207.14 |
| 4,417,574 | 11/1983 | Talonn et al. | 128/205.12 |
| 4,457,305 | 7/1984 | Shanks et al. | 128/205.27 |
| 4,566,480 | 1/1986 | Parham | 128/205.24 |
| 4,598,704 | 7/1986 | Bordoni et al. | 128/200.18 |
| 4,742,823 | 5/1988 | Bird | 128/203.12 |
| 4,792,097 | 12/1988 | Kremer, Jr. et al. | 128/200.21 |
| 4,805,609 | 2/1989 | Roberts et al. | 239/338 |
| 4,825,859 | 5/1989 | Lambert | 128/207.14 |

FOREIGN PATENT DOCUMENTS 1488249 10/1977 United Kingdom ........... 128/200.14

Primary Examiner—Edgar S. Burr
Assistant Examiner—Kimberly Asher

[57] ABSTRACT

A pressurized ventilation system to supplement patient respiration which enables introduction and atomization of prescribed liquids and removal of condensation while maintaining pressurization and functions of the ventilation system and minimizing hazards due to contamination. An atomizer outlet is positioned to enable entrainment of atomized particles of the prescribed liquid into the breathable gas flowing to the patient. A novel arrangement of a valve and conduit provides for contamination-free attachment of a syringe or unit dose vial for the introduction of the prescribed liquid. An enclosure means for trapping condensate and control means for safe removal of condensate from the system are provided. The ventilation system, with the improved arrangement, provides novel functions and can be operated and maintained more conveniently and expeditiously than prior art ventilator system while reducing the risk of infection for both the patient and the attendant.

5 Claims, 3 Drawing Sheets

PRESSURIZED MEDICAL VENTILATION SYSTEM

This application is a continuation-in-part of copending application Ser. No. 07/311,959 entitled "PRESSURIZED VENTILATION APPARATUS FOR PATIENT" filed Feb. 17, 1989, which is a continuation-in-part of application Ser. No. 07/074,867 entitled "PRESSURIZED VENTILATION SYSTEM FOR PATIENTS" filed Jul. 17, 1987 now U.S. Pat. No. 4,805,609 and owned by the present applicant.

The present invention relates to the arrangement of a pressurized ventilator system to supplement respiration for a patient, including an atomizer for atomizing prescribed liquids into the breathable gas delivered into the patient. The arrangement of this invention enables condensation to be removed and prescribed liquids to be introduced, while maintaining pressure and function of the system and reducing contamination for the attendant and patient.

Some patients in modern intensive care units require control or augmentation of breathing. Normally, a positive-pressure ventilation system is used to provide breathable gas, such as an oxygen-enriched gas, under positive pressure to the patient. Some patients are so dependent on pressurized ventilation that disconnection or leakage in the system can be life threatening. Such loss of pressure may be caused by structural leaks or errors in operation that have often resulted from the need to periodically open the system to remove condensate or introduce prescribed liquids to be atomized and inhaled by the patient.

Gas is delivered to a ventilation system through the gas-flow and inspiration-rate controller. The breathable gas flows through a main supply conduit from the controller to the patient. The atomizer is usually part of a device, called a nebulizer, which contains a reservoir for prescribed liquids and is connected within the main supply conduit. The prescribed liquids are atomized using breathable gas supplied from a separate connection on the gas-flow and inspiration-rate controller, to provide the same total amount of breathable gas to the patient whether the atomizing gas is turned on or off. When the atomizing gas is turned off, the nebulizer acts as a water trap accumulating condensed water in the reservoir.

Formerly, in order to administer atomizer treatments, the attendant was required to open the system by removing the cup-like reservoir which formed the bottom of the nebulizer. This resulted in depressurizing and complete loss of function of the ventilator system until the reservoir was properly reattached. The opening of the system and the subsequent procedure resulted in cross-contamination into and out of the ventilator system. Before the reservoir could be reattached to the nebulizer apparatus, the condensate had to be emptied from the reservoir and the prescribed dosage introduced quickly in order to minimize the disconnect time. This requirement to perform quickly often resulted in incomplete removal of condensate, spillage, dropping of the cup-like chamber, and consequent delays. Furthermore, if the reservoir was improperly reattached, it resulted in an ongoing leak in the system.

Total loss of pressure and oxygen enrichment, which occurred during such procedures caused an alteration in the cardiopulmonary dynamics, which at times resulted in hypoxemia, bradycardia or cardiac arrhythmias and destabilization of the patient. For some patients, a dramatic deterioration in vital signs occurred when the system was depressurized, even momentarily.

The present invention helps to minimize the risks enumerated above, as well as other risks associated with the use of prior art systems. These, and other contributions of the invention, are considered in more detail by reference to the accompanying drawing, wherein.

The present invention provides a nebulizing apparatus which enables atomizer treatments to be administered without opening or depressurizing the system, thus protecting both the patient and attendant from contamination; and without disturbing the preset positive pressure level, oxygen enrichment, or the volume of breathable gas provided.

Figure 1:
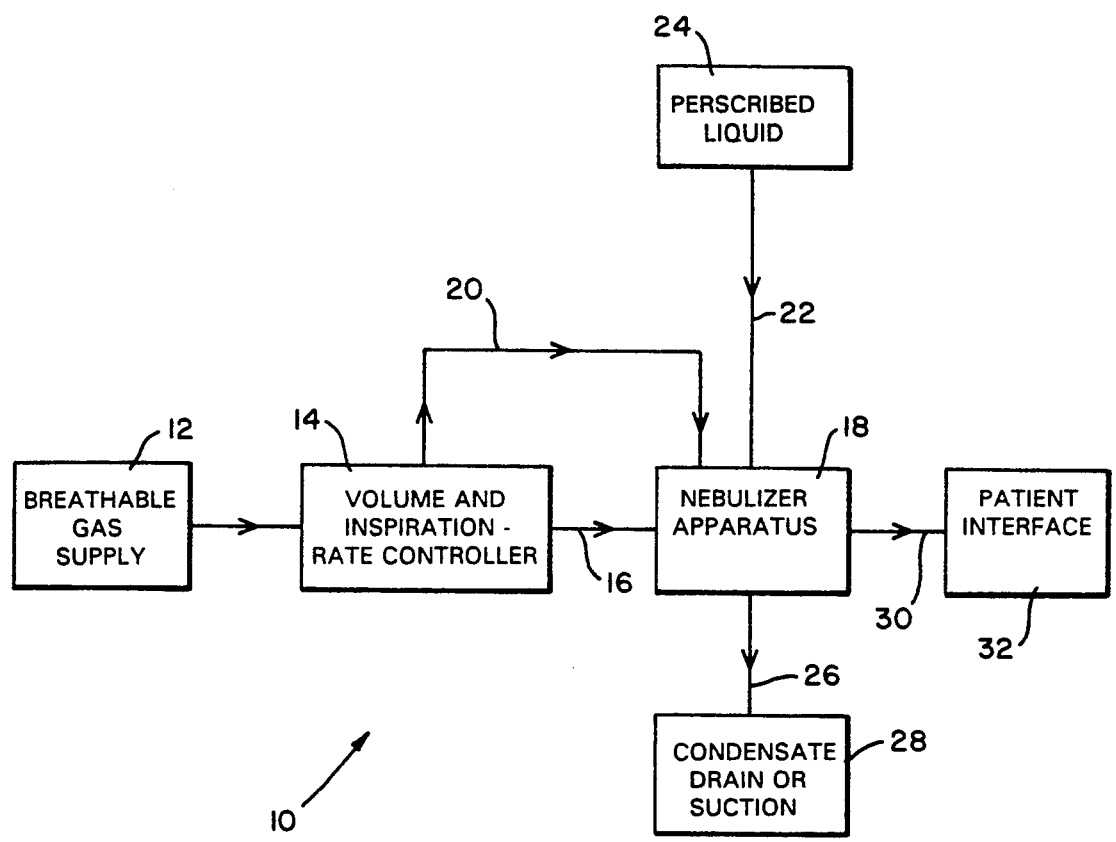
FIG. 1 is a block diagram for describing the arrangement of the major components for the pressurized medical ventilation system of this invention.

The pressurized ventilation system 10 of this invention, shown schematically in FIG. 1, comprises the following components: The breathable gas source 12 provides gas to a gas-flow and inspiration-rate controller 14, which provides humidification, heating and bacterial filtration in a manner well-known in the art. Conduit 16 directs the main flow of breathable gas to the patient through nebulizer apparatus 18. Conduit 20 provides breathable gas for atomizing prescribed liquids in the nebulizer apparatus and forms part of the controlled flow of breathable gas to the patient. Conduit 22 enables a source of prescribed liquids 24 to be connected to the system for controlled introduction of the prescribed liquids 24. Conduit 26 provides controlled removal of condensate from the nebulizer apparatus to a drain or suction 28.

Medicated, breathable gas flows from the nebulizer 16 through the conduit 30 to patient interface apparatus 32 which comprises an adaptor to the endotracheal tube inserted into the patients airway, an exhalation valve controlled by the gas-flow and inspiration-rate controller to close during inspiration and open during expiration. Such patient interface apparatus are well-known in the art and not critical to understanding this invention.

Figure 2:
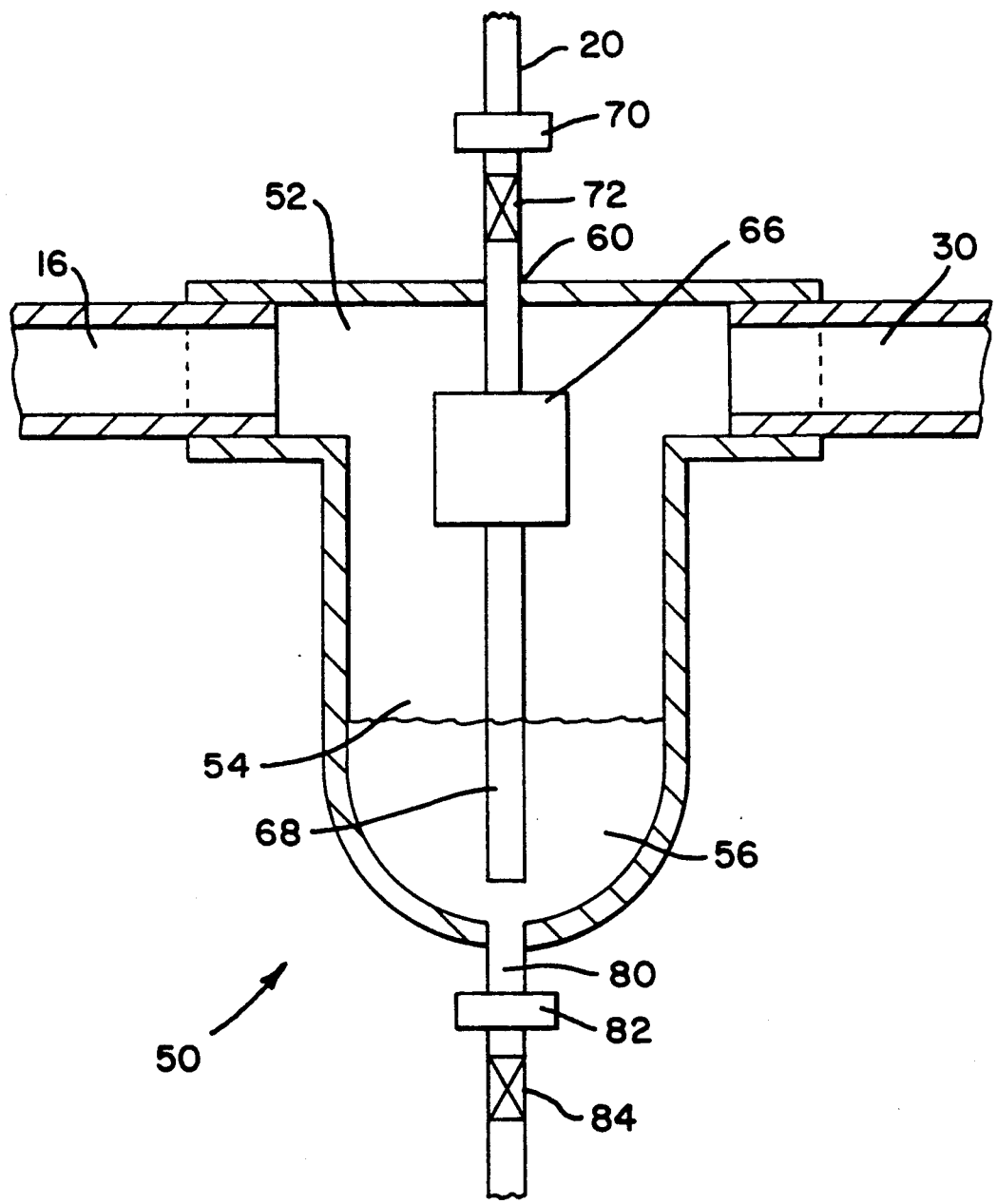
FIG. 2 is a schematic sectional view of the preferred embodiment of the nebulizing apparatus of the invention showing the improved access and control for removing condensate from and adding prescribed liquid to a reservoir.

FIG. 2 shows an embodiment of the nebulizing apparatus of this invention 50. Components of the apparatus work together to provide controlled and safe access for removing condensate and adding prescribed liquids to be atomized and supplied to the breathable gas flowing to the patient without depressurizing the system.

Chamber 52, through which the main conduit 16,30 directs the breathable gas, forms a reservoir 54 containing a liquid 56—either prescribed liquids when the nebulizer is on or condensate collecting when the nebulizer is off. Conduit 20 conducts gas to atomizer 66 for atomizing prescribed liquids. In the atomizer, a gas nozzle creates an air jet blowing across the end of intake tube 68. The resulting venturi effect draws prescribed liquids through intake tube 68 into the gas jet stream, atomizing the liquid into the breathable gas, in a manner well known in the art.

Connected within conduit 20 luer-type screw connector 70 and a check valve 72 enable prescribed liquids to be introduced into the nebulizer reservoir through the nebulizer gas supply conduit. To add prescribed liquids, conduit 20 is disconnected from connector 70 and a syringe or unit/metered dose vial (not shown) is connected while the check valve 72 allows the medicine to be pushed into the system, as well as preventing any gas from flowing out of the system.

Conduit 80 conducts condensate from the bottom of the reservoir, through connector 82 and valve 84 to a drain or suction. Connector 82 is preferably a luer type screw connector. Valve 84 is a tube-clamping type valve attached to the conduit, eliminating the risk of the valve being accidentally left open.

Figure 3:
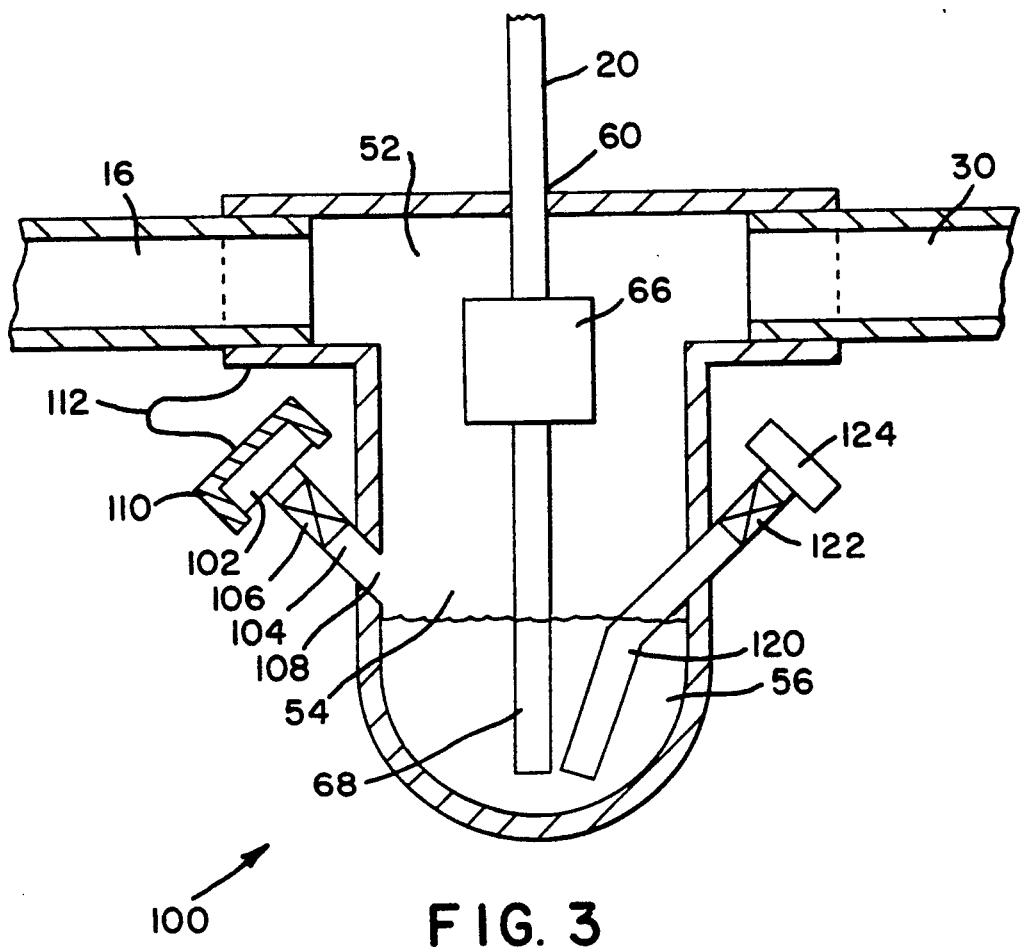
FIG. 3 is a schematic sectional view showing another embodiment of the nebulizing apparatus of the invention showing the improved access and control for removing condensate from and adding prescribed liquid to a reservoir.
Figures 4, 5:
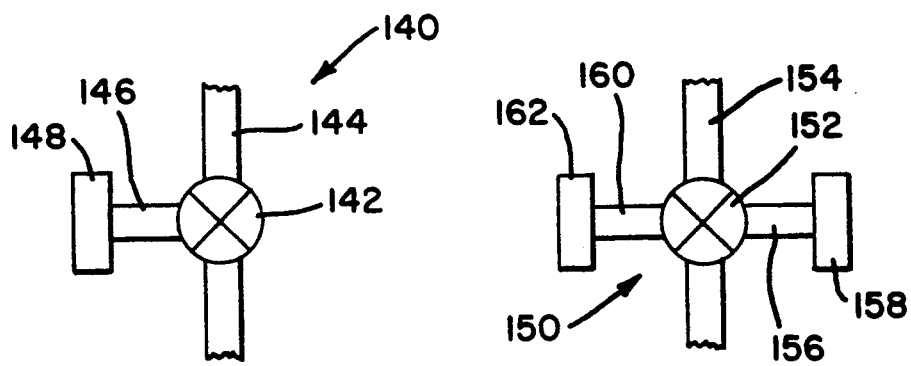
FIG. 4 is a schematic sectional view showing an alternate control means in the form of a three-way valve.
FIG. 5 is a schematic sectional view showing an alternate control means in the form of a four-way valve.

FIG. 3 shows an alternative embodiment of the nebulizing apparatus of this invention 100. Prescribed liquid is introduced through connector 102 into conduit 104 which contains check valve 106. The conduit terminates at port 108 which is in communication with the reservoir. Cap 110 provides an additional seal and protects the connector 102 from contamination when no syringe or unit/metered dose vial is attached. A cap holder string 112 is attached to the cap and some other part of the system.

FIG. 3 also shows conduit 120 in communication with the bottom of the reservoir, for removing condensate. The conduit terminates at a suction connector comprising of valve 122 with integral connector 124.

The conduit for liquid medicine 104 is shown connected directly to the shell of the nebulizing device; however, it could be connected as a branch within the nebulizing gas conduit 20 or within the condensate removing conduit 120.

The specific embodiments disclosed above can use more complex means for controlling access. FIG. 4 shows control means 140 in the form of a three-way valve 142 within conduit 144. Branching conduit 146 terminates at a luer-type screw connector 148. FIG. 5 shows control means 150 in the form of a four-way valve 152 within conduit 154. Branching conduit 156 terminates at a luer-type screw connector 158, and branching conduit 160 terminates at connector 162. Additional control means such as a check valve can be connected within such branching conduits. Control means as shown in FIG. 4 or FIG. 5 can be connected within conduits for introducing prescribed liquids or removing condensate disclosed above to enable attachment of a unit/metered dose vial for introducing prescribed liquids or a syringe for either introducing prescribed liquids or removing condensate in a controlled manner. For example the specific embodiment of FIG. 2 can use a control means in the form shown in FIG. 4 or FIG. 5 connected within the atomizing gas conduit, enabling the attachment of a syringe or unit/metered dose vial without disconnecting the atomizing gas. As another example the specific embodiment of FIG. 2 could use a control means in the form shown in FIG. 4 or FIG. 5 connected within the condensate conduit to enable the introduction of prescribed liquids through the condensate conduit to eliminate the need for connector 70 and valve 72.

Plastic materials useful in fabricating elements described above are available in the art; and, specifics as to such plastics or fabrication methods are not necessary to the understanding of this invention. While this invention has been described with specific structural relationships, and particular materials, it will be appreciated that variations within the spirit and scope of the invention can be made by those skilled in the art in the light of the above disclosure, so that the scope of the present invention is to be determined by reference to the following claims.

I claim:

1. A patient treatment apparatus comprising:
   - a positive-pressure hermetically sealed ventilator system for control of patient respiration;
   - and said ventilator having means providing a source of pressurized breathable gas;
   - a patient interface structure;
   - a main conduit defining a main flow path having a first end connected to said source and a second end connected to said patient interface structure;
   - said ventilator having a respiration/breathing control means for control of the flow of breathable gas into and/or out of the patient's respiratory system;
   - a nebulizer bowl for the storage of a medicine and having an one end in communication with a segment of said main conduit for defining a chamber along said flow path;
   - an atomizer located in said chamber and having an inlet to receive said medicine and an outlet for delivering an atomized medicine into said flow path;
   - said chamber having at least one port;
   - a removal conduit connected to said port for removing fluids from said bowl while maintaining the positive pressure in said system;
   - a check valve located across said removal conduit;
   - a source of pressurized gas for said atomizer;
   - a second conduit having a first end leading from said source of pressurized gas for said atomizer and having its exhaust end in said chamber located at an area to cause a negative pressure of sufficient degree to draw said medicine from said bowl;
   - a one-way check valve located across said second conduit; and
   - first pump means for delivering medicine into said bowl through said second conduit while maintaining positive pressure in said system.

2. The invention of claim 1 wherein said second conduit has a fixture intermediate its length at a location wherein said check valve is between said fixture and said chamber and wherein the outer end of said second conduit is connected to either said source of pressurized gas or to said first pump means through said fixture.

3. A patient treatment apparatus comprising:
   - a positive-pressure hermetically sealed ventilator system for control of patient respiration;
   - and said ventilator system having means providing a source of pressurized breathable gas;
   - a patient interface structure;
   - a main conduit defining a flow path having a first end connected to said source and a second end connected to said patient interface structure;
   - said ventilator having a respiration/breathing control means for control of the flow of breathable gas into and/or out of the patient's respiratory system;
   - a nebulizer bowl for the storage of a medicine and having an one end in communication with a segment of said main conduit for defining a chamber along said flow path, and said chamber having a first port in a wall of said chamber;

a feed conduit having an inner end connected to said first port and having an outer end;

a one-way check valve between said first port and said outer end;

a fitting at said outer end to receive a positive displacement means for delivering medicinal liquid into said bowl;

an atomizer located in said chamber and having an inlet to receive said medicine from said first port and an outlet for delivering an atomized medicine into said flow path;

said chamber having at least one drainage port;

a drainage conduit connected to said drainage port for removing fluids from said bowl while maintaining the positive pressure in said system;

a check valve located across said conduit;

a source of pressurized gas for said atomizer;

a second conduit having a first end leading from said source of pressurized gas for said atomizer and having its exhaust end in said chamber located at an area to cause a negative pressure of sufficient degree to draw said medicine from said bowl;

a one-way check valve located across said second conduit; and first pump means for delivering medicine into said bowl through said fitting while maintaining positive pressure in said system.

4. A patient treatment apparatus comprising:

a positive-pressure hermetically sealed ventilator system for control of patient respiration;

and said ventilator system having means providing a source of pressurized breathable gas;

a patient interface structure;

a main conduit defining a main flow path having a first end connected to said source and a second end connected to said patient interface structure;

said ventilator having a respiration/breathing control means for control of the flow of breathable gas into and/or out of the patient's respirator system;

a nebulizer bowl for the storage of a medicine and having an one end in communication with a segment of said main conduit for defining a chamber along said flow path;

an atomizer located in said chamber and having an inlet to receive said medicine and an outlet for delivering an atomized medicine into said flow path;

said chamber having at least one port;

a removal conduit connected to said port for removing fluids from said bowl while maintaining the positive pressure in said system;

a check valve located across said removal conduit;

a source of pressurized gas for said atomizer;

a second conduit having a first end leading from said source of pressurized gas and having its exhaust end in said chamber located at an area to cause a negative pressure of sufficient degree to draw said medicine from said bowl;

a three-way check valve is disposed across said second conduit; and first pump means for delivering medicine into said bowl through said second conduit while maintaining positive pressure in said system.

5. A patient treatment apparatus comprising:

a positive-pressure hermetically sealed ventilator system for control of patient respiration;

and said ventilator system having means providing a source of pressurized breathable gas;

a patient interface structure;

a main conduit defining a main flow path having a first end connected to said source and a second end connected to said patient interface structure;

said ventilator having a respiration/breathing control means for control of the flow of breathable gas into and/or out of the patient's respirator system;

a nebulizer bowl for the storage of a medicine and having an one end in communication with a segment of said main conduit for defining a chamber along said flow path;

an atomizer located in said chamber and having an inlet to receive said medicine and an outlet for delivering an atomized medicine into said flow path;

said chamber having at least one port;

a removal conduit connected to said port for removing fluids from said bowl while maintaining the positive pressure in said system;

a check valve located across said removal conduit;

a source of pressurized gas for said atomizer;

a second conduit having a first end leading from said source of pressurized gas and having its exhaust end in said chamber located at an area to cause a negative pressure of sufficient degree to draw said medicine from said bowl;

a four-way check valve is disposed across said second conduit; and first pump means for delivering medicine into said bowl through said second conduit while maintaining positive pressure in said system.

* * * * *

UNITED STATES PATENT AND TRADEMARK OFFICE
CERTIFICATE OF CORRECTION

PATENT NO. : 5,119,807

DATED : June 9, 1992

INVENTOR(S) : Josephine A. Roberts, Jephthae W. Burwell

It is certified that error appears in the above-identified patent and that said Letters Patent is hereby corrected as shown below:

Column 5, line 43 "respirator" should be --respiratory--.

Column 6, line 27 "respirator" should be --respiratory--.

Signed and Sealed this

Twenty-eighth Day of September, 1993

*Attest:*

*Attesting Officer*

BRUCE LEHMAN

*Commissioner of Patents and Trademarks*